United States Patent [19]
Marrone et al.

[11] Patent Number: 5,869,042
[45] Date of Patent: Feb. 9, 1999

[54] METHODS FOR CONTROLLING ABOVE-GROUND PLANT DISEASES USING ANTIBIOTIC-PRODUCING BACILLUS SP. ATCC 55608 OR 55609

[75] Inventors: Pamela Gail Marrone; Sherry D. Heins, both of Davis; Desmond R. Jiménez, Woodland, all of Calif.

[73] Assignee: AgraQuest, Inc., Davis, Calif.

[21] Appl. No.: 755,060

[22] Filed: Nov. 22, 1996

[51] Int. Cl.$^6$ .......................... A01N 63/00; A01N 33/00; C12P 13/00; C12N 1/20
[52] U.S. Cl. ..................... 424/93.46; 435/128; 435/158; 435/252.5; 435/834; 514/579; 514/740
[58] Field of Search ................... 435/252.5, 128, 435/158, 834; 424/93.46, 93.461; 514/579, 740

[56] References Cited

U.S. PATENT DOCUMENTS

| | | | |
|---|---|---|---|
| 5,049,379 | 9/1991 | Handelsman et al. | 424/115 |
| 5,061,495 | 10/1991 | Rossall | 424/520 |
| 5,552,138 | 9/1996 | Handelsman et al. | 424/93.46 |
| 5,736,382 | 4/1998 | Handelsman et al. | 435/252.5 |

FOREIGN PATENT DOCUMENTS

| | | |
|---|---|---|
| WO 94/09630 | 5/1994 | WIPO . |
| WO 95/24126 | 9/1995 | WIPO . |
| WO 96/08504 | 3/1996 | WIPO . |
| WO 96/39483 | 12/1996 | WIPO . |

OTHER PUBLICATIONS

Schwinn et al., "Control with chemicals" Advances in Plant Pathology: vol. 7: *Phytophtothora infestans*, the Cause of Late Blight of Potato, Ingram et al., eds., Academic Press, San Diego, (1991) 8:225–265.

Campbell, *Biological Control of Microbial Plant Pathogens* (1989), Cambridge University Press, New York, p. 77.

Stabb et al., "Zwittermicin A—producing strains of *Bacillus cereus* from diverse soils" *Appl. Envrion. Microbiol.* (1994) 60:4404–4412.

Milner et al., "Production of Kanosamine by *Bacillus cereus* UW85" *Appl. Environ. Microbiol.* (1996) 62:3061–3065.

He et al., "Zwittermicin A, and antifungal and plant protection agent from *Bacillus cereus*" *Tetra. Lett.* (1994) 35:2499–2502.

Osburn et al., "Effect of *Bacillus cereus* UW85 on the yield of soybean at two field sites in Wisconsin" *Am. Phytopatol. Soc.* (1995) 79:551–556.

Smith et al., "Suppression of cottony leak of cucumber with *Bacillus cereus* strain UW85" *Plant Disease* (1993) 77:139–142.

Leifert et al., "Antibiotic production and biocontrol activity by *Bacillus subtilis* CL27 and *Bacillus pumilus* CL45" *J. Appl. Bacteriol.* (1995) 78:97–108.

McKeen et al., "Production and partial characterization of antifungal substances antagonistic to *Monilinia fructicola* from *Bacillus subtilis*" *Phytopathol.* (1986) 76:136–139.

*Primary Examiner*—David M. Naff
*Attorney, Agent, or Firm*—Morrison & Foerster, LLP

[57] ABSTRACT

Above-ground fungal and bacterial infections of plants are treated by applying to the plants an antibiotic-producing *Bacillus sp.* strain ATCC 55608, 55609, 53522 and/or zwittermicin-A antibiotic therefrom. The above-ground infections treated can be caused by *Phytophthora infestans, Botrytis cinerea, Pseudomonas syringae, Alternaria solani, Plasmopara viticola, Uncinula necator, Puccinia recondita f.sp. Tritici, Staganospora nodorum, Monilinia fructicola* or *Erwinia herticola*. The *Bacillus sp.* and/or antibiotic when applied can be in the form of a whole culture broth, an antibiotic-containing supernatant, a powder, granules, a concentrate, an aqueous suspension or a microencapsulated formulation.

26 Claims, No Drawings

METHODS FOR CONTROLLING ABOVE-GROUND PLANT DISEASES USING ANTIBIOTIC-PRODUCING BACILLUS SP. ATCC 55608 OR 55609

TECHNICAL FIELD OF THE INVENTION

The present invention is in the field of biopesticides. More particularly, this invention describes the use of antibiotic-producing bacteria to control above-ground plant fungal and bacterial diseases such as those caused by *Phytophthora infestans* (late blight), *Alternaria solani* (early blight), *Plasmopara viticola* (downy mildew), *Uncinula necator* (powdery mildew), *Puccinia recondita f.sp. tritici* (leaf rust), *Stagnospora nodorum* (glume blotch), *Pseudomonas syringae* (bacterial speck), *Botrytis cinerea* (gray mold), *Erwinia herbicola* (bacterial blight) and *Monilinia fructicola* (brown rot).

BACKGROUND OF THE INVENTION

Above-ground plant diseases are common in a wide variety of plants. These diseases are often caused by fungal or bacterial infections including infestations of *Phytophthora infestans* (late blight), *Alternaria solani* (early blight), *Plasmopara viticola* (downy mildew), *Uncinula necator* (powdery mildew), *Puccinia recondita f.sp. tritici* (leaf rust), *Stagnospora nodorum* (glume blotch), *Pseudomonas syringae* (bacterial speck), *Botrytis cinerea* (gray mold), *Erwinia herbicola* (bacterial blight) and *Monilinia fructicola* (brown rot). *Phytophthora infestans* (*P. infestans*) or "late blight" is best known as the fungus which caused the Irish potato famine. More than a century after it destroyed Ireland's potato crops, late blight is still a potentially devastating infestation affecting potato and tomato crops. The signs of a *P. infestans* infection include large, dark green, water-soaked spots on the plant's leaves and large, dark brown spots on the fruit or tuber. If left untreated, the leaves die and the potato or tomato rots.

*Botrytis cinerea* (*B. cinerea*), also known as gray-mold disease, is common on soft, ripe fruits (e.g., strawberries, raspberries); vegetables (e.g., lettuce, tomato, artichoke, asparagus); legumes (e.g., lima beans, kidney beans) and ornamental plants (e.g., african violet, begonia, carnation, rose, poinsettia). Signs associated with this fungal disease include a brown or gray dusty mold covering the fruit, stems or leaves.

To date, control of above-ground fungal or bacterial pathogens has been limited to treatment with synthetic chemical pesticides. Many chemical fungicides are classified as carcinogens by the EPA. Many of these chemicals are also toxic to wildlife and other non-target species. In addition, pathogens may often develop resistance to chemical pesticides. (See, e.g., Schwinn et al., p. 244, ADVANCES IN PLANT PATHOLOGY: PHYTOPHTHORA INFESTANS, THE CAUSE OF LATE BLIGHT OF POTATO (Academic Press, San Diego 1991)).

Biological control offers an attractive alternative or addition to present disease-control practices. It is safer for the environment and less expensive to produce. Biological control of above-ground diseases is, however, particularly challenging because the surface of a plant provides a difficult environment for the introduction, survival and multiplication of biological control agents such as bacteria. (See, e.g., Campbell, R., p.77, BIOLOGICAL CONTROL OF MICROBIAL PLANT PATHOGENS (Cambridge Univ. Press, New York 1989)). Thus, few commercially viable biocontrol agents are currently available for the control of above-ground plant disease. *Bacillus subtilis* is used commercially as a seed treatment (Kodiak™), however, *Bacillus sp.* are not employed for above-ground plant diseases.

Naturally-occurring fungicidal bacterial strains are relatively uncommon. Screening programs have identified certain *Bacillus sp.* (*B. sp.* includes *B. subtilis, B. cereus, B. mycodies, B. anthracis* and *B. thuringiensis*) strains which exhibit antifungal activity. (See, e.g., Stabb et al. (1990) *Applied Environ. Microbiol.* 60(12):4404–4412). These strains have been shown to produce zwittermicin-A and/or "antibiotic B," now known as kanosamine (Milner et al. (1996) *Appl. Environ. Microbiol.* 62:3061–3065), two antibiotic agents which are effective against the soil borne disease "damping-off" caused by *Phytophthora medicaginis, Phytophthora nicotianae, Phytophthora aphanidermatum* or *Sclerotinia minor.* (See, Stabb et al., supra).

Zwittermicin A is a water-soluble, acid-stable linear aminopolyol molecule. (See, He et al. (1994) *Tetra. Lett.* 35(16) :2499–2502). U.S. Pat. No. 5,049,379 to Handelsman et al. describes how zwittermicin A-producing *B. cereus* can be used to control the below-ground seedling diseases "root rot" and "damping off" in alfalfa and soybean. When the seed is coated with zwittermicin-A produced by *B. cereus* ATCC 53522, the pathogenic activity of the root rot fungus is inhibited. Similarly, application of spore-based formulations of certain *B. cereus* strains to soybean seeds or the soil surrounding the seeds has been shown to improve soybean yield at field sites. (See, Osburne et al. (1995) *Am. Phytopathol. Soc.* 79(6): 551–556).

Smith et al. (1993) *Plant Disease* 77(2):139–142 report that the activity of the soil-borne fungus, *Pythium aphandiermatum,* that causes cottony cucumber leak can be suppressed using zwittermicin-producing *B. cereus* strain UW85. Liefert et al. (1995) *J. Appl. Bacteriol.* 78:97–108 report the production of anti-Botrytis and anti-*Alternaria brassicicola* antibiotics by two Bacillus strains, *B. subtilis* CL27 and *B. pumilis* CL45. The whole broth and cell-free filtrates were active against Botrytis and Alternaria in in vitro tests and were active against Botrytis in in vivo small plants tests on Astilbe. The authors identified three antibiotics produced by the *B. subtilis* strain CL27, two of which were thought to be peptides and one non-peptide. Unlike the bacterial strains of the present invention, the antibiotics produced by the *B. pumilis* strain CL45 demonstrated only in vitro activity, no in vivo activity was demonstrated.

A lipoprotein antibiotic having a molecular weight of approximately 63,500 daltons that demonstrates activity against gram-positive bacteria but not gram-negative bacteria is disclosed in U.S. Pat. No. 5,061,495. In addition, this antibiotic is active against wheat powdery mildew caused by *Erysiphe graminis* and *Botrytis fabae.* McKeen et al. (1986) *Phytopathol.* 76:136–139 report the use of *B. subtilis* and antibiotics produced by *B. subtilis* for control of peach brown rot.

However, there have been no other reports of antibiotic-producing *Bacillus sp.* strains effective against pathogens responsible for above-ground plant diseases. Thus, there remains a need for biocontrol agents which are effective against above-ground fungal and bacterial infections.

DISCLOSURE OF THE INVENTION

A method of treating or protecting plants from above-ground fungal and bacterial infections comprising the step of applying an effective amount of an antibiotic-producing *Bacillus sp.* bacterial strain within the present invention, wherein the bacterial strain is selected from the group consisting of AQ175 having ATCC Accession No. 55608, AQ177 having ATCC Accession No. 55609 and AQ178 having ATCC Accession No. 53522. The antibiotic-producing Bacillus sp. bacterial strain can be provided as a cell suspension in a whole broth culture. Also provided are methods of treating or protecting plants by applying an antibiotic-containing supernatant obtained from a whole broth culture of an antibiotic-producing Bacillus. sp. bacterial strain within the present invention. Methods of treating or protecting plants from above-ground fungal and bacterial diseases comprising applying cell suspension in whole broth cultures or supernatants obtained from more than one antibiotic-producing Bacillus sp. bacterial strain within the present invention are also provided.

MODES OF CARRYING OUT THE INVENTION

The present invention comes from the novel finding that certain antibiotic-producing bacterial strains are effective in treating and protecting plants from above-ground fungal and bacterial infections. Thus, the invention includes methods of preventing and treating above-ground fungal and bacterial diseases in plants using the bacterial strains selected from the group consisting of AQ175 having ATCC Accession No. 55608, AQ177 having ATCC Accession No. 55609 and AQ178 (ATCC No. 53522) or antibiotic-containing supernatants obtained from these bacterial strains.

In one aspect, the invention comprises applying an effective amount of antibiotic-producing bacterial strain AQ175, AQ177 or AQ178 to a plant in order to prevent or treat above-ground fungal and bacterial infections. The bacterial strain can be provided as a cell suspension in a whole broth culture. In another aspect, the invention encompasses preventing or treating above-ground fungal and bacterial infections by applying an effective amount of an antibiotic-containing supernatant obtained from one of the antibiotic-producing bacterial strains. In another aspect, more than one of the antibiotic-producing bacterial strains AQ175, AQ177 and AQ178 are applied in order to prevent or treat above-ground fungal and bacterial infections of plants. Whole broth cell suspension of these bacterial strains or antibiotic-containing supernatants obtained from cultures of these bacterial strains or combinations thereof can be applied to such plants. In addition, purified antibiotics produced by either of these bacterial strains can be applied to plants in an effective amount to treat or prevent above-ground fungal and bacterial disease. In addition, other antibiotic-producing bacterial strains may be combined with the antibiotic-producing bacterial strains of the present invention for use in treating or preventing above-ground fungal and bacterial plant disease. Further aspects of the invention are described below.

DEFINITIONS

As used herein, "biological control" is defined as control of a pathogen by the use of a second organism. Known mechanisms of biological control include enteric bacteria which control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

The term "fungus" or "fungi" includes a wide variety of nucleated, sporebearing organisms which are devoid of chlorophyll. Examples of fungi include yeasts, mildews, molds, rusts, and mushrooms.

The term "bacteria" includes any prokaryotic organism that does not have a distinct nucleus.

"Fungicidal" means the ability of a substance to increase mortality or inhibit the growth rate of fungi.

"Antibiotic" includes any substance which is able to inhibit or kill a microorganism. Antibiotics may be produced by another microorganism or by a synthetic or semisynthetic process. The term, therefore, includes a substance which inhibits or kills fungi, for example, zwittermicin-A.

The term "culturing" refers to the propagation of organisms on or in media of various kinds. "Whole broth culture" refers to a liquid culture containing both cells and media. "Supernatant" refers to the liquid broth remaining when cells grown in broth are removed by centrifugation, filtration, sedimentation or other means well known in the art.

An "effective amount" is an amount sufficient to effect beneficial or desired results. An effective amount can be administered in one or more administrations. In terms of treatment and protection, an "effective amount" is that amount sufficient to palliate, ameliorate, stabilize, reverse, slow or delay the progression of fungal or bacterial disease states.

Unlike known treatments for above-ground plant diseases, the method of this invention employs biocontrol agents to control fungal and bacterial infections. Thus, in one aspect, the present invention entails a method of treating or protecting a plant from fungal and bacterial infections comprising the step of applying an effective amount of an antibiotic-producing bacterial strain within the present invention, specifically strains AQ175, AQ177 or AQ178 to the plant.

The bacterial strains of this invention may be grown in any conventional growth medium that supports Bacillus sp. Examples of suitable broth for culturing Bacillus sp. include, but are not limited to, a broth composed of peptone, dextrose, yeast extract, malt extract, proflo cottonseed extract and soy flour and a broth made of half-strength trypticase soy broth. Solid substrates are also suitable for growing Bacillus sp. Growth procedures may also be readily scaled up to large fermentors by methods well known in the art.

In one embodiment, the antibiotic-producing bacterial strain is applied as a suspension in a whole broth culture wherein the concentration of a bacterial strain within the present invention is between $2 \times 10^7$ and $4 \times 10^7$ CFU/mL. The broth may be diluted to 25% of full strength, preferably it is used at greater than 50% full strength, more preferably at greater than 75% full strength and even more preferably at full strength. In preferred embodiments, the bacterial suspension provides protection from or treatment of the above-ground fungal or bacterial infections caused by P. infestans (late blight), B. cinerea (gray-mold), P. syringae (bacterial speck), Uncinula necator, Plasmopara viticola, Stagnospora tritici and Puccinia recondita.

In another aspect, the antibiotic-producing bacterial strain of the present invention is selected from the group consisting of AQ175 (ATCC No. 55608), AQ177 (ATCC No. 55609) and AQ178 (ATCC No. 53522). Strains AQ175, AQ177 and AQ178 were previously shown to produce the fungicide zwittermicin A. (Stabb et al., supra.).

In another aspect, the present invention provides a method of protecting and treating plants from above-ground fungal and bacterial infections comprising applying an effective amount of a supernatant obtained from a whole broth culture of an antibiotic-producing bacterial strain within the present invention. The supernatant may be obtained by means well known in the art including centrifugation, filtration, sedimentation or the like. The supernatant may be used immediately, refrigerated or frozen for future use. The supernatant may be diluted to 25% full strength, preferably it is used at greater than 50% fill strength, more preferably at greater than 75% full strength and even more preferably at full strength.

In another aspect, the invention encompasses a method of protecting and treating plants from above-ground fungal and bacterial infections comprising applying an effective amount of a biocontrol agent selected from the group consisting of bacterial cells of antibiotic-producing bacterial strains within the present invention, whole broth cultures of such strains and supernatant obtained from an antibiotic-producing bacterial strain. Moreover, the invention encompasses a method of protecting and treating plants from above-ground fungal and bacterial infections comprising applying an effective amount of both bacterial strains within the present invention in the form of whole broth cultures, supernatants and/or cells. Thus, a spectrum of above-ground plant diseases can be treated in one application.

In order to achieve good dispersion and adhesion of the whole broth cultures and antibiotic-containing supernatants within the present invention, it may be advantageous to formulate the whole broth cultures and the supernatants with components that aid dispersion and adhesion. Suitable formulations will be known to those skilled in the art.

The antibiotic-containing supernatants and whole broth cultures and compositions comprising at least one antibiotic and at least one culture of an antibiotic-producing bacterial strain can be formulated as wettable powders, soluble powders, soluble powders in wettable granules, dry flowables, aqueous flowables, wettable dispersible granules, emulsifiable concentrates, aqueous suspensions, and the like, or can be microencapsulated in a suitable medium, or liquid or solid formulations. (See, e.g., U.S. Pat. No. 5,061, 495 to Rossall or U.S. Pat. No. 5,049,379 to Handlesman). Suitable formulations will be known to those skilled in the art.

All patents and publications cited herein are incorporated by reference.

The following examples are provided to illustrate the invention. These examples are not to be construed as limiting.

EXAMPLES

Example 1
AQ175 and AQ177 Produce Zwittermicin-A

Bacterial strains known to produce zwittermicin-A exhibit synergistic effects with *Bacillus thuringiensis*. (see, Manker et al. WO/9409630). Therefore, to determine whether AQ175 and AQ177 produce zwittermicin-A, cultures of these strains were mixed with Javelin® (*B. thuringiensis*) and observed for synergistic activity. More specifically, 50 mL cultures of AQ175 and AQ177 were grown in TSB for three days at 29° C. The whole broth cultures were centrifuged at 4,200 g for 20 minutes. The supernatants were decanted and stored at −20° C. One mL of each supernatant was used as a stock, while one mL was diluted with 500 µl of sterile distilled water. Eight serial dilutions were then made from the diluted sample.

Javelin® WG (0.0521 g) was mixed with 50 mL of distilled water to produce a 1000 µg/mL stock solution. The stock solution was then serially diluted in distilled water to give eight 0.5 mL solutions. A 50:50 mixture of the Javelin® stock solution and each supernatant stock solution were then serially diluted and then transferred to a 96-well microplate. 40 µl aliquots of each dilution were dispensed into the wells of a microplate containing 200 µl/well of artificial diet. The samples were dried at room temperature and 5–10 synchronized beet armyworm eggs suspended in 25 µl of a 1% agar were added to each well. The egg agar was allowed to dry, and the plates covered with perforated Mylar®. After seven days, the number of live insects in each sample well was tabulated. Results are shown in Table 1.

TABLE 1

| AQ175 and AQ177 Enhancement of Javelin | | | | | | | | |
|---|---|---|---|---|---|---|---|---|
| | Javelin ® concentration (µg) | | | | | | | |
| | 41.6 | 27.4 | 18.1 | 12 | 7.9 | 5.2 | 3.4 | 2.3 |
| Javelin alone (#1) | 1$^a$s$^b$ | 1s | 3s | 5s | 11 | 14 | 13 | 22 |
| Javelin alone (#2) | 1s | 2s | 3s | 6s | 17 | 22 | 19 | 17 |
| Jav + AQ175 | nd | 0 | 0 | | 0 | 0 | 2s | 5s |
| Jav + AQ177 | nd | 0 | 0 | 0 | 0 | 0 | 4s | 9s |

$^a$All numbers in this table are the number of living insects.
$^b$The "s" indicates that the living insects were extremely stunted compared to controls.

The results show that when AQ175 and AQ177 supernatant was combined with *B. thuringiensis*, Javelin®, the synergistic effect characteristic of zwittermicin is seen.

Example 2
Antibiotic Activity in Culture

To determine if the zwittermicin-producing bacterial strains AQ175, AQ177 and AQ178 were effective against the fungi *Phytophthora infestans* (*P. infestans*) and *Botrytis cinerea* (*B. cinerea*), the following experiment was performed. Petri plates were filled with an agar medium (PDA—potato dextrose agar, Difco). Cultures of *P. infestans* or *B. cinerea* were grown for three days in liquid YPG-1 medium (0.4% yeast extract, 0.1% $KH_2PO_4$, 0.05% $MgSO_4 \cdot 7H_2O$, 1.5% glucose). A 0.1 mL aliquot of spore suspension (concentration approximately $2 \times 10^6$ spores/mL) of pathogen was spread onto the agar.

The bacterial strains used for this experiment are described in Stabb et al. (1994) *Appl. Environ. Microbiol.* 60(12):4404–4412. For all data reported the "AQ#" corresponds to the strains described in Stabb as follows: AQ175= DGA-34, AQ177=AS4-12 and AQ178=UW85.

Bacterial strains AQ175, AQ177 and AQ178 were grown in half-strength trypticase soy broth (15 g TSB/liter of water, Difco) for three days. To test whole broth cultures, the strains were grown to a concentration of approximately $1 \times 10^6$ to $6 \times 10^6$ CFU/mL and aliquots taken from these cultures. Supernatant was obtained by density centrifugation of the cultures at 5,200 rpm for 20 minutes.

Cultures of *Phytophthora infestans* and *Botrytis cinerea* were grown for three days in liquid YPG-1 medium (0.4% yeast extract, 0.1% $KH_2PO_4$, 0.05% $MgSO_4 \cdot 7H_2O$, 1.5% glucose). Aliquots of 0.1–0.2 mL of spore suspension (concentration approximately $2 \times 10^6$ spores/mL) of pathogen were spread onto an agar medium (potato dextrose agar (PDA), Difco) in petri plates.

Two 7 mm holes were made in each petri dish. A volume of 100 µL of test sample (either supernatant or whole broth) was added to each 7 mm hole. Each test was performed in duplicate. No microorganism test sample was added to a control plate. The zone of inhibition, measured in millimeters, of *P. infestans* or *B. cinerea* growth around each hole was measured after 3 to 10 days. Results for *P. infestans* are shown in Table 2 and for *B. cinerea* in Table 3. Control plates showed no zone of inhibition.

TABLE 2

| P. infestans | | | |
|---|---|---|---|
| | AQ175 | AQ177 | AQ178 |
| Supernatant | 11 | 11 | 11 |
| Whole broth | 12 | 11 | 11 |

TABLE 3

| B. cinerea | | | |
|---|---|---|---|
| | AQ175 | AQ177 | AQ178 |
| Supernatant | nz | 15 | 11 | nz = no zone (note, AQ177 and AQ178 inhibited Botrytis in this test)

To determine the in vitro effectiveness of whole broth aliquots of AQ175 and AQ177 against *Alternaria solani*, the same methodology as described here in Example 2 was employed. AQ175 did not inhibit *Alternaria solani* but AQ177 gave an 11 mm zone. The test was repeated in 96-well microplates and gave the following results: AQ175 exhibited 30% inhibition while AQ177 exhibited 70% inhibition. Both whole broth and supernatant of the zwittermicin-producing strains inhibited the growth of the pathogen *P. infestans* in vitro. Both AQ177 and AQ178 also exhibited inhibitory effects on *B. cinerea*.

To determine in vitro effectiveness of these strains against the fungi *Erwinia herbicola* and *Monilinia fructicola*, the following experiment was conducted. Bacterial strains were cultured as described above. *Monilinia fructicola* cultures were grown on V-8 agar (20 g agar, 4 g $CaCO_3$, 200 mL V-8 juice) in the dark at room temperature for 8 days. Spores were harvested by placing sterile distilled water on the surface of the culture plates and scraping the surface with a sterile needle to dislodge the spores. Spore concentration was adjusted to $3.3 \times 10^6$ spores/mL and 400 μl added to 4 mL of soft potato dextrose agar. This mixture was poured over the surface of potato dextrose agar culture places and the soft agar allowed to solidify. *Erwinia herbicola* was fermented overnight in half-strength TSA and $1 \times 10^5$ cells were spread on a TSA agar plate. Using a sterile no. 4 cork borer, 5 wells were made in each plate and 100 μl of a three day old culture of AQ175 and AQ177 were added to each well. Plates were incubated at room temperature in the dark and the zones of no growth of the around each well measured. Results are summarized in Table 4.

TABLE 4

| Bacterial inhibition of *M. fructicola* and *E. herbicola* | | |
|---|---|---|
| | *M. fructicola* | *E. herbicola* |
| AQ175 | 9 mm | 9 mm |
| AQ177 | 0 | 9 mm |
| Water | 0 | 0 |

These results demonstrate that AQ175 inhibited growth of *M. fructicola*, and both strain AQ175 and AQ177 inhibited *E. herbicola* growth.

Example 3
Antibiotic Activity Using Whole Plants

The ability of zwittermicin-producing bacterial strains to control late blight (*P. infestans*) infection was tested on whole tomato plants. Tomato plants (Ace variety) were purchased from Ace hardware and transplanted into 6 packs having three plants per pack. Bacterial strain AQ178 was grown to approximately $10^7$ CFU/mL in a cotton seed extract medium (peptone, dextrose, yeast, soy and proflo, Trader's Protein). *P. infestans* cultures were prepared as described in Example 1. Three tomato plants (1 pack) were sprayed to runoff with a whole broth culture of AQ178, and then air-dried at approximately 70° F. Three control plants were untreated. All plants were then sprayed to runoff with a *P. infestans* culture at $1.55\times10^5$ CFU/mL. The plants were air-dried at 70° F., lightly misted with de-ionized water, enclosed in a clear plastic bag and incubated at approximately 16° C. The amount of late blight infestation was recorded three and seven days after treatment. Results are shown in Table 5.

TABLE 5

| | Untreated Controls (% leaves infected) | AQ178 treated plants (% leaves infected) |
|---|---|---|
| Day 3 after treatment | 50 | 0 |
| Day 7 after treatment | 100 | 5.9 |

Treatment of plants with whole broth cultures of strain AQ178 gave complete control of late blight, *Phytophthora infestans,* three days after treatment, and nearly complete control seven days after treatment.

Example 4

Dose Dependent Antibiotic Activity of AQ178 Whole Broth and Supernatant

Bacterial cultures were grown as described in Example 2 and either whole broth cultures or supernatants were prepared. Tomato plants and *P. infestans* were prepared as described in Example 2, except that the plants were sprayed with varying dosages of either whole broth cultures or with supernatant prior to spraying with *P. infestans.* The amount of late blight infestation was recorded ten and seventeen days after treatment. Results are shown in Tables 6 and 7.

TABLE 7

| Light blight infection ten days after treatment with AQ178 | | |
|---|---|---|
| Dose | Whole Broth Percent Infected Leaves | Supernatant Percent Infected leaves |
| 25% | 77.8 | 14.3 |
| 50% | 25.0 | 14.3 |
| 75% | 0 | 0 |
| 100% | 0 | 0 |
| Light blight infection seventeen days after treatment with AQ178 | | |
| Dose | Whole Broth Percent Infected Leaves | Supernatant Percent Infected Leaves |
| 25% | 77.8 | 14.3 |
| 50% | 41.2 | 49.6 |
| 75% | 8.5 | 8.5 |
| 100% | 0 | 34.7 |

Untreated Control plants showed 33% infection

AQ178 provided complete control of late blight, *Phytophthora infestans* at 75% and full strength whole broth cultures and supernatant ten days post treatment. At seventeen days post treatment, whole broth cultures outperformed supernatant.

Example 5

Dose Dependent Antibiotic Activity of AQ177 Whole Broth and Supernatant

Tomato plants (Ace and Patio varieties) were transplanted into 6 packs having three plants per pack. AQ177 grown in half strength trypticase soy broth (15 g TSB, Difco, in 1 liter of water) for 72 hours and reached a concentration of 5×106 CFU/mL. One plant of each variety of tomato plant was sprayed to runoff with a whole broth culture or supernatant of AQ177. As shown in Table 8, whole broth cultures of AQ177 grown in half-strength trypticase soy broth gave complete protection of plants seven days after treatment. Whole broth cultures provided more protection than supernatant.

TABLE 8

Light blight infection seven days after treatment with AQ177

| Percent of full strength | Whole Broth (% leaf infection/ % petiole infection) | Supernatant (% leaf infection/% petiole infection) |
|---|---|---|
| 50% | 0/0 | Not done |
| 75% | 0/0 | 23/0 |
| 100% | 0/0 | 0/0 |

Untreated Control = 39/50

Example 6
Antibiotic Activity of AQ175 and AQ177

To assay the effects of the bacterial strains on tomato plant varieties, the procedure described in Example 5 was performed on either the Ace or Patio varieties of tomato plants. AQ175 and AQ177 were grown in TSB (Difco) for 72 hours and reached concentrations of $2.5 \times 10^7$ cells/mL and $3.6 \times 10^7$ cells/mL, respectively. The tomato plants were sprayed to runoff with the different bacterial strains and the plants were scored for both leaf infection with late blight and evidence of bacterial speck. Results are shown in Table 9.

TABLE 9

Light blight and bacterial speck infection fifteen days after treatment with AQ175 or AQ177

| Bacterial strain - Tomato Plant Ace (A) Patio (P) | Whole Broth or Supernatant | # infected leaves/# of leaves | Percent Infection | Bacterial Speck Infection |
|---|---|---|---|---|
| AQ175 (A) | supernatant | 1\37 | 2.7 | on |
| AQ175 (P) | supernatant | 1\34 | 2.9 | any |
| Average |  |  | 2.8 | treatments |
| AQ175 (A) | whole broth | 2\34 | 5.9 |  |
| AQ175 (P) | whole broth | 2\28 | 7.1 |  |
| Average |  |  | 6.5 |  |
| AQ177 (A) | supernatant | 2\33 | 6.1 |  |
| AQ177 (P) | supernatant | 4\30 | 13.3 |  |
| Average |  |  | 9.7 |  |
| AQ177 (A) | whole broth | 6\35 | 17.1 |  |
| AQ177 (P) | whole broth | 4\33 | 12.1 |  |
| Average |  |  | 14.6 |  |
| Phytophthora untreated control |  |  |  |  |
| (A) |  | 6\26 | 23.1 | 100% covered with speck Full of bacterial speck |
| (P) |  | 4\32 | 12.5 | Full of bacterial speck |
| Average |  |  | 17.8 |  |

These results show that the antibiotic-producing strains within the present invention are effective against late blight and bacterial speck.

Example 7
Antibiotic Activity of AQ175, AQ177 and AQ178 Against *B. cinerea*

To test the effectiveness of the antibiotic-producing bacterial strains of the present invention against *B. cinerea*, fresh strawberries picked the day of testing were utilized. For test #1, frozen supernatant of AQ177 or AQ178 was used. The AQ177 supernatant was grown in trypticase soy broth (TSB) as described in Example 1. The AQ178 supernatant was grown in cotton seed extract medium (proflo, dextrose, peptone, Trader's Protein). In test #2, AQ175 was grown in either half-strength TSB or in potato dextrose broth (PDB) and the broth or supernatant tested without freezing. Whole broth cultures and supernatants were sprayed onto the strawberries until runoff, then allowed to air dry.

*B. cinerea* spores were grown on potato dextrose agar in a petri plate and scraped into de-ionized water to form a liquid inoculum. The *B. cinerea* inoculum, measuring approximately $5.8 \times 10^5$ cells per mL was sprayed onto the berries until runoff, and the berries allowed to air dry. In test #1, the berries were placed inside a cardboard container with plastic wrap lid at 25° C. In test #2, all berries were place uncovered in an incubator at approximately 16° C. Results are shown in Table 10.

TABLE 10

| Botrytis test Bacterial strain | No. Strawberries per treatment | # infected/# clean |
|---|---|---|
| Test #1 |  |  |
| 178 frozen supernatant | 3 | 2/1 |
| 177 frozen supernatant | 3 | 1/2 |
| Untreated Control | 3 | 3/0 |
| Test #2 |  |  |
| 175(PDB) whole broth | 2 | 0/2 |
| 175(PDB) supernatant | 2 | 1/1 |
| 175(TSB) whole broth | 2 | 0/2 |
| 175(TSB) supernatant | 2 | 0/2 |
| Untreated control | 2 | 1/1 |

AQ177 and AQ178 frozen supernatants were effective in reducing *B. cinerea* infection in whole plants. In addition, whole broth cultures of AQ175 were completely effective at preventing *B. cinerea* infection, regardless of the medium used. While supernatant from AQ175 grown in potato dextrose broth did not prevent infection, supernatant from the same strain grown in TSB was 100% effective against *B. cinerea*.

Example 8
Antibiotic Activity of AQ175 and AQ177 Against Fungal Pathogens

To test the antibiotic-producing bacterial strains of the present invention against a number of fungal pathogens, the strains were grown in half-strength TSB. Cells were cultured to between $5 \times 10^6$ and $9.8 \times 10^8$ cells/mL. Replicates of three test plants and three control plants per pathogen were utilized. The test plants were each sprayed with a whole broth culture of an antibiotic-producing bacterial strain to run-off with a hand-held sprayer. When the foliage had dried, each test plant was sprayed a second time. After the second application of the bacterial strain culture has dried, the test plants and the control plants were inoculated with the appropriate fungal pathogen. Plants were incubated under conditions conducive to disease development. In addition, positive controls were utilized by testing known pesticides against appropriate fungal pathogens in the same manner as the cultures of the bacterial strains were tested. Each plant was evaluated by estimating the percent disease control using a scale from 0% control to 100% control. (0=disease level of untreated control; 100=plants with no visible lesions). The fungal pathogens, resulting diseases, host plant and control pesticides are presented in Table 11. The results are shown in Table 12.

TABLE 11

| Disease | Pathogen | Host Plant | Standard Pesticide |
|---|---|---|---|
| Late Blight | Phytophthora infestans | tomato | metalaxyl |
| Early Blight | Alternaria solani | tomato | propiconazole |
| Gray Mold | Botrytis cinerea | pepper | propiconazole |
| Downy Mildew | Plasmopara viticola | grape | metalaxyl |
| Powdery Mildew | Uncinula necator | grape | propiconazole |
| Leaf Rust | Puccinia recondita f.sp. tritici | wheat | propiconazole |
| Glume Blotch | Staganospora nodorum | wheat | propiconazole |

TABLE 12

| | Rate | % disease control | | | | | | |
|---|---|---|---|---|---|---|---|---|
| Treatment | (ppm) | Pi[y] | As | Pv | Un | Bc | Sn | Pr |
| AQ175 | — | 37 | 0 | 33 | 90 | 100 | 88 | 30 |
| AQ177 | — | 47 | 92 | 0 | 98 | 100 | 98 | 40 |
| metalaxyl | 30 | 90 | — | 100 | — | — | — | — |
| | 20 | — | — | 67 | — | — | — | — |
| | 10 | 47 | — | — | — | — | — | — |
| myclobutanil | 10 | — | — | — | 100 | — | — | — |
| | 1 | — | — | — | 0 | — | — | — |
| propiconazole | 250 | — | 93 | — | — | — | — | — |
| | 30 | — | 37 | — | — | — | — | — |
| | 10 | — | — | — | — | 100 | 100 | — |
| | 15 | — | — | — | — | 63 | 73 | 95 |
| | 1 | — | — | — | — | — | — | 33 |
| Disease Index (%)[z] | — | 50 | 80 | 75 | 30 | 80 | 80 | 80 |

[y] Pi = P. infestans, As = A. solani, Pv = P. viticola, Un = U. necator, Bc = B. cinerea, Sn = S. nodorum, Pr = P. recondita f.sp. tritici.
(%)[z] Disease index = percent diseased tissue on the untreated, inoculated plants.

Both bacterial strains provided complete control of B. cinerea. AQ177 provided the highest level of control against the greatest number of fungal pathogens. AQ175 exhibited similar activity to AQ177 but showed no activity against P. viticola and A. solani. Both bacterial strains were particularly active against grape pathogens. Combinations of the bacterial strains are useful to protects against common diseases in certain crops.

Example 9

Activity of AQ175 and AQ177 Versus Post-Harvest Brown Rot. Monilinia fructicola 250 mL cultures of AQ175 and AQ177 were grown for 3.5 days. AQ175 and AQ177 were grown in one-half strength TSB as described in Example 5. Peaches were surface sterilized with a 10% bleach (Chlorox) solution, rinsed with deionized water and air dried. Whole broth cultures of AQ175 ($7.0 \times 10^5$ CFU/mL) and AQ177 ($6.0 \times 10^6$ CFU/mL) were sprayed with a hand-held sprayer on two peaches each until runoff (approximately 50 mL per two peaches). The peaches were allowed to dry. Monilinia spores were scraped from a petri plate and suspended in deionized water to obtain a concentration of $1.09 \times 10^5$ spores/mL. The peaches were sprayed with the spore suspension until runoff and allowed to air dry. Two peaches were untreated and two peaches were sprayed with Monilinia, but not with either whole broth culture. The peaches were placed in a polypropylene container in an incubator in the dark at 18° C.

After four days incubation, the amount of brown rot was observed and recorded. The following results were obtained:

| AQ175 peach 1 | 4.5 × 2.5 cm lesion |
|---|---|
| AQ175 peach 2 | no infection |
| AQ177 peach 1 | 3 × 1.5 cm lesion |
| AQ177 peach 2 | no infection |
| Untreated peach 1 | 9 × 7 cm lesion |
| Untreated peach 2 | 3 × 2 cm lesion |
| Monilinia only peach 1 | 7 × 5 cm lesion |
| Monilinia peach 2 | 4 × 3 cm lesion |

The results show that both AQ175 and AQ177 suppressed Monilinia brown rot on peaches compared to the untreated control and the Monilinia-only peaches. The treatments with AQ175 and AQ177 had only one peach each with brown rot and the size of the lesions was much smaller than the untreated and Monilinia-only controls.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows the scope of the appended claims.

What is claimed is:

1. A method for treating to protect plants from above-ground fungal and bacterial infections, comprising applying to the plant an effective amount of the antibiotic-producing Bacillus spp bacterial strain selected from the group consisting of AQ175 having ATCC Accession No. 55608 and AQ177 having ATCC Accession No. 55609.

2. The method of claim 1 wherein the infection is caused by Phytophthora infestans.

3. The method of claim 1 wherein the infection is caused by Botrytis cinerea.

4. The method of claim 1 wherein the infection is caused by Pseudomonas syringae.

5. The method of claim 1 wherein the infection is caused by Alternaria solani.

6. The method of claim 1 wherein the infection is caused by Plasmopara viticola.

7. The method of claim 1 wherein the infection is caused by Uncinula necator.

8. The method of claim 1 wherein the infection is caused by Puccinia recondita f.sp. tritici.

9. The method of claim 1 wherein the infection is caused by Staganospora nodorum.

10. The method of claim 1 wherein the infection is caused by Monilinia fructicola.

11. The method of claim 1 wherein the infection is caused by Erwinia herbicola.

12. The method of claim 1 wherein the antibiotic-producing Bacillus sp. bacterial strain is applied to the plant as a whole broth culture.

13. The method of claim 12 wherein the culture is diluted.

14. The method of claim 1 wherein the antibiotic is zwittermicin-A.

15. The method of claim 1 wherein said bacterial strain is applied as a wettable powder, soluble powder, soluble powder in wettable granules, wettable dispersible granules, emulsifiable concentrate, aqueous suspension, or microencapsulated formulation.

16. The method according to claim 1 wherein the bacterial strain is applied in an aqueous flowable form or a dry flowable form.

17. A method for treating to protect plants from above-ground fungal and bacterial infections, comprising applying to the plant an effective amount of at least one antibiotic produced by the antibiotic-producing *Bacillus spp* bacterial strain selected from the group consisting of AQ175 having ATCC Accession No. 55608 and AQ177 having ATCC Accession No. 55609.

18. The method of claim 17 wherein the antibiotic is applied to the plant as a supernatant.

19. The method of claim 18 wherein the supernatant is diluted.

20. The method of claim 18 wherein the supernatant is refrigerated or frozen prior to application to the plant.

21. The method of claim 17 wherein the antibiotic is zwittermicin-A.

22. The method of claim 16 wherein said antibiotic is applied as a wettable powder, soluble powder, soluble powder in wettable granules, wettable dispersible granules, emulsifiable concentrate, aqueous suspension, or microencapsulated formulation.

23. The method according to claim 17 wherein the bacterial strain is applied in an aqueous flowable form or a dry flowable form.

24. A method for treating to protect plants from above-ground fungal and bacterial infections, comprising applying to the plant an effective amount of at least one antibiotic-producing *Bacillus spp.* bacterial strain selected from the group consisting of AQ175 having ATCC Accession No. 55608 and AQ177 having ATCC Accession No. 55609 and at least one antibiotic produced by either said bacterial strain.

25. The method of claim 24 wherein said bacterial strain and said antibiotic are applied as wettable powders, soluble powders, soluble powders in wettable granules, wettable dispersible granules, emulsifiable concentrates, aqueous suspensions or microencapsulated formulation.

26. The method according to claim 24 wherein the bacterial strain and the antibiotic are applied in an aqueous flowable form or a dry flowable form.

* * * * *